United States Patent
Dicosimo et al.

(12) 
(10) Patent No.: US 6,670,158 B2
(45) Date of Patent: Dec. 30, 2003

(54) METHOD FOR PRODUCING METHACRYLIC ACID ACRYLIC ACID WITH A COMBINATION OF ENZYME CATALYSTS

(75) Inventors: Robert Dicosimo, Rockland, DE (US); Robert D. Fallon, Elkton, MD (US); John E. Gavagan, Wilmington, DE (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 130 days.

(21) Appl. No.: 10/067,652

(22) Filed: Feb. 5, 2002

(65) Prior Publication Data
US 2003/0148480 A1 Aug. 7, 2003

(51) Int. Cl.$^7$ ............... C12P 13/00; C12P 7/40; C12N 1/20
(52) U.S. Cl. .......... 435/128; 435/136; 435/252.1
(58) Field of Search ............... 435/136, 128, 435/252.1

(56) References Cited

U.S. PATENT DOCUMENTS

| | | |
|---|---|---|
| 5,135,858 A | 8/1992 | Yamada et al. |
| 5,998,180 A | 12/1999 | Armitage et al. |
| 6,162,624 A | 12/2000 | Symes et al. |

FOREIGN PATENT DOCUMENTS

| | | |
|---|---|---|
| EP | 187680 A2 | 7/1986 |

OTHER PUBLICATIONS

W. Bauer, Jr. Methacrylica Acid and Derivatives: in: Ullmann's Encyclopedia of Industrial Chemistry, 5$^{th}$ Ed.; Eds; B. Elvers, S. Hawkins, G. Schultz; VCH, New York, 1990; vol. A16, pp 441–452.
A. W. Gross, J. C. Dobson, Methacrylic Acid and Derivatives: in: Kirk–Othmer Encyclopedia of Chemical Technology, 4$^{th}$ Ed.; Eds: J. I. Kroschwitz, M. Howe–Grant; John Wiley and Sons, New York, 1995; vol. 16, pp. 474–506.
T. Ohara et al., "A crylic Acid and Derivatives" in: Ullmann's Encyclopedia of Industrial Chemistry, 5$^{th}$ Ed., Ed: W. Gerhartz; VCH, New York, 1985; vol. A1, pp. 161–176.
W. Bauer, "Acrylic Acid and Derivatives" in: Kirk–Othmer Encyclopedia of Chemical Technology, 4$^{th}$ Ed., J. I> Kroschwitz, M. Howe–Grant; John Wiley and Sons, New York, 1991; vol. 1, pp. 287–314.
Nagasawa et al., Appl. Microbiol. Biotechnol. 34: 322–324, 1990.
Webster et al., Biotechnology Letters, 23: 95–101, 2001.
Meth–Cohn et al., J. Chem. Soc., Perkin Trans. 1, 1099–1104, 1997.
Appl. Biochem. Biotechnol., 77–79: 671–679, 1999.
Appl. Microbiol. Biotechnol., 40: 189–195, 1993.

Primary Examiner—Herbert J. Lilling

(57) ABSTRACT

The invention provides a process for the hydrolysis of acrylonitrile to acrylic acid, and for the hydrolysis of methacrylonitrile to methacrylic acid, in high yield and at high concentration with high specificity. Acrylonitrile or methacrylonitrile is hydrolyzed in a suitable aqueous reaction mixture by a catalyst characterized by a nitrile hydratase and amidase activity of Comamonas testosteroni 5-MGAM-4D, producing the corresponding acid. The acrylic acid or methacrylic acid is isolated as the acid or corresponding salt.

6 Claims, No Drawings

METHOD FOR PRODUCING METHACRYLIC ACID ACRYLIC ACID WITH A COMBINATION OF ENZYME CATALYSTS

FIELD OF THE INVENTION

The invention provides a process for the hydrolysis of acrylonitrile to acrylic acid, and for the hydrolysis of methacrylonitrile to methacrylic acid, in high yield and at high concentration with high specificity. Acrylonitrile or methacrylonitrile is hydrolyzed in a suitable aqueous reaction mixture by an enzyme catalyst characterized by the nitrile hydratase and amidase activities of *Comamonas testosteroni* 5-MGAM-4D, producing the corresponding carboxylic acid. The acrylic acid or methacrylic acid is isolated as the acid or corresponding salt.

BACKGROUND OF THE INVENTION

Methacrylic acid and its esters are widely used to produce acrylic sheet, molding products, coatings and impact modifiers, and in applications that include use in detergent builders, rheology modifiers, oil additives, solventless inks, paints, polishes, and coatings. Although several manufacturing processes to produce methacrylic acid exist, the hydrolysis of methacrylamide sulfate (produced from acetone cyanohydrin) accounts for the majority of current commercial production worldwide (W. Bauer, Jr. "Methacrylic Acid and Derivatives" in: Ullmann's Encyclopedia of Industrial Chemistry, 5$^{th}$ Ed.; Eds: B. Elvers, S. Hawkins, G. Schulz; VCH, New York, 1990; vol. A 16, pp 441–452; A. W. Gross, J. C. Dobson, "Methacrylic Acid and Derivatives" in: Kirk-Othmer Encyclopedia of Chemical Technology, 4$^{th}$ Ed.; Eds: J. I. Kroschwitz, M. Howe-Grant; John Wiley and Sons, New York, 1995; vol. 16, pp 474–506). In this process, approximately 1.6 kg of sulfuric acid is required to produce 1 kg of methacrylic acid via methacrylamide sulfate. Therefore, alternative processes to eliminate sulfuric acid recycle and regeneration (and the significant energy resources required) in current commercial processes for methacrylic acid production are highly desirable.

Methacrylic acid may also be prepared via the ammoxidation of isobutylene to give methacrylonitrile, which is then hydrolyzed to methacrylamide by treatment with one equivalent of sulfuric acid. The methacrylamide can be hydrolyzed to methacrylic acid under conditions similar to those used in the acetone cyanohydrin-based process (Gross et al. supra).

Acrylic acid is primarily used as an intermediate in the production of acrylates, which in turn are used in the production of coatings, finishes, paints, adhesives, and in the manufacture of superabsorbents and detergent builders. Most commercial acrylic acid is produced by the oxidation of propylene. An alternate route to acrylic acid is based on the hydrolysis of acrylonitrile (produced by ammoxidation of propylene) by sulfuric acid. This process is not practiced commercially because of the costs associated with the large amounts of ammonium sulfate waste which is generated (T. Ohara et al., "Acrylic Acid and Derivatives" in: Ullmann's Encyclopedia of Industrial Chemistry, 5$^{th}$ Ed.; Ed: W. Gerhartz; VCH, New York, 1985; vol. A1, pp 161–176; W. Bauer, "Acrylic Acid and Derivatives" in: Kirk-Othmer Encyclopedia of Chemical Technology, 4$^{th}$ Ed.; Eds: J. I. Kroschwitz, M. Howe-Grant; John Wiley and Sons, New York, 1991; vol. 1, pp 287–314).

Microbial catalysts capable of hydrolyzing methacrylonitrile to methacrylic acid, or acrylonitrile to acrylic acid, do not produce the undesirable ammonium sulfate waste stream that results when using sulfuric acid for this purpose. *Rhodococcus rhodochrous* J1 nitrilase has been used to produce acrylic acid and methacrylic acid from acrylonitrile and methacrylonitrile, respectively (Nagasawa et al., *Appl. Microbiol. Biotechnol.* 34:322–324 (1990)). This enzyme exhibited marked inhibition when the acrylonitrile concentration was higher than 200 mM, and the conversion rate of methacrylonitrile to methacrylic acid was low when compared to acrylic acid production; for hydrolysis of acrylonitrile, reactions were run with constant monitoring of acrylonitrile concentration, and periodic feeding of acrylonitrile over the course of the reaction was required to maintain the concentration below 200 mM. U.S. Pat. No. 5,135,858 describes the use of nitrilase enzyme from Rhodococcus to convert acrylonitrile to acrylic acid, and methacrylonitrile to methacrylic acid. The specific activity of *R. rhodochrous* J1 nitrilase for methacrylonitrile was only 8% of the specific activity for acrylonitrile.

U.S. Pat. Nos. 5,998,180 and 6,162,624 disclose the use of Rhodococcus nitrilase enzymes for the hydrolysis of acrylonitrile to acrylic acid, and methacrylonitrile to methacrylic acid, where the nitrilase enzymes each have a Km of 500 μM or below and a Ki of at least 100 mM. In U.S. Pat. No. 5,998,180, it is disclosed that the reaction is preferably performed by maintaining an upper concentration limit of acrylonitrile or methacrylonitrile of 175 mM over the course of the reaction by constant feeding of acrylonitrile. In U.S. Pat. No. 6,162,624, acrylonitrile or methacrylonitrile has an upper concentration limit of 1 or 2 wt % or less, often 0.5 wt % or less, and preferably 0.2 wt % or less, where acrylonitrile or methacrylonitrile is constantly fed over the course of the reaction. The very low concentration of (meth) acrylonitrile present in the reactor necessitates careful control of reactant concentration, in particular for fed batch, and especially for continuous processes.

A recent comparison of two Rhodococcus isolates as catalysts for ammonium acrylate production (one with only a nitrilase activity, and one with only a combination of nitrile hydratase and amidase activities) concluded that the catalyst having a combination of nitrile hydratase and amidase activities was less preferred due to (a) difficulty in inducing the two enzymes in the required ratio, (b) the susceptibility of the two enzymes (nitrile hydratase and amidase) to deactivation by acrylonitrile, and (c) inhibition of the two enzymes by the respective products (Webster et al., *Biotechnology Letters*, 23:95–101 (2001)).

European Patent Appl. EP 187680 A2 discloses the hydrolysis of acrylonitrile and methacrylonitrile to the corresponding acids using Nocardia, Bacillus, Brevibacterium, Micrococcus, Bacteridium, and Corynebacterium, where light irradiation of the microbial catalysts was required to increase the reaction rate 10–20 fold. Hydrolysis of 200 mM methacrylonitrile by Rhodococcus sp. AJ270 gave the corresponding acid in almost quantitative yield, whereas hydrolysis of acrylonitrile produced acrylic acid in only ca. 70% yield under the same conditions (Meth-Cohn et al., *J. Chem. Soc., Perkin Trans.* 1, 1099–1104 (1997)).

Microbial catalysts containing only a nitrile hydratase which have been used for the hydration of acrylonitrile to acrylamide are also often susceptible to inactivation by high concentrations of acrylonitrile. Padmakumar and Oriel (*Appl. Biochem. Biotechnol.*, 77–79:671–679 (1999)) reported that Bacillus sp. BR449 expresses a thermostable nitrile hydratase, but when used for hydration of acrylonitrile to acrylamide, inactivation of the enzyme occurred at concentration of acrylonitrile of only 2 wt %, making this catalyst unsuitable for commercial applications. Nagasawa et al. (*Appl. Microbiol. Biotechnol.*, 40:189–195 (1993)) compare the three microbial nitrile hydratase catalysts which have been used for commercial production of acrylamide from acrylonitrile. Compared to the nitrile hydratase activity of *Rhodococcus rhodochrous* J1, the nitrile hydratase activity of Brevibacterium R312 and *Pseudomonas chlororaphis* B23 catalysts was not stable above 10° C., and the nitrile hydratase activity of all three catalysts was sensitive to the concentration of acrylonitrile in the reaction, where inactivation of the nitrile hydratase occurs at higher concentrations. In commercial use, the concentration of acrylonitrile was maintained at 1.5–2 wt % when using Brevibacterium R312 and *P. chlororaphis* B23 catalysts, while a concentration of up to 7 wt % was used with *R. rhodochrous* J1.

Developing an industrial process using microbial catalysts having nitrilase or nitrile hydratase/amidase activities to efficiently manufacture acrylic and methacrylic acid has proved difficult. Many methods using enzyme catalysts to prepare acrylic acid or methacrylic acid from the corresponding nitrites do not produce and accumulate a product at a sufficiently high concentration to meet commercial needs, or are subject to enzyme inactivation (requiring a low concentration of nitrile over the course of the reaction) or product inhibition during the course of the reaction.

The problem to be solved continues to be the lack of facile microbial catalysts to convert acrylonitrile or methacrylonitrile to the corresponding acids in a process characterized by high yield, high concentration, and high selectivity, and with the added advantages of low temperature and energy requirements and low waste production when compared to known chemical methods of nitrile hydrolysis.

SUMMARY OF THE INVENTION

The invention provides a process for the hydrolysis of acrylonitrile to acrylic acid, and for the hydrolysis of methacrylonitrile to methacrylic acid in high yield and at high concentration with high specificity. The invention has the steps of (a) contacting acrylonitrile or methacrylonitrile in a suitable aqueous reaction mixture with a catalyst characterized by nitrile hydratase and amidase activities of *Comamonas testosteroni* 5-MGAM-4D (ATCC 55744), to produce the corresponding carboxylic acid; and (b) isolating the acrylic acid or methacrylic acid produced in (a) as the acid or corresponding salt.

A further embodiment of the invention uses a catalyst having nitrile hydratase and amidase activities of *Comamonas testosteroni* 5-MGAM-4D in the form of intact microbial cells, permeabilized microbial cells, one or more cell components of a microbial cell extract, and partially-purified enzyme(s), or purified enzyme(s).

In any form, the catalysts may be immobilized in or on a soluble or insoluble support.

BRIEF DESCRIPTION OF THE BIOLOGICAL DEPOSITS

Applicants have made the following biological deposit under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| *Comamonas testosteroni* 5-MGAM-4D | ATCC 55744 | 8 Mar. 1996 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Applicants have solved the stated problem by providing a process to prepare acrylic acid or methacrylic acid from the corresponding nitriles in high yield and at high concentration with high specificity by using a catalyst having a combination of nitrile hydratase and amidase activities. The process has the added advantages of low temperature and energy requirements and low waste production relative to previously known methods. Acrylic acid and methacrylic acid produced by the present invention have useful applications in many industrial processes and products.

Microbial catalysts can hydrolyze a nitrile directly to the corresponding carboxylic acids using a nitrilase (EC 3.5.5.7), where there is no intermediate production of the corresponding amide (Equation 1), or by a combination of nitrile hydratase (EC 4.2.1.84) and amidase (EC 3.5.1.4) enzymes, where a nitrile hydratase (NHase) initially converts a nitrile to an amide, and then the amide is subsequently converted by the amidase to the corresponding carboxylic acid (Equation 2):

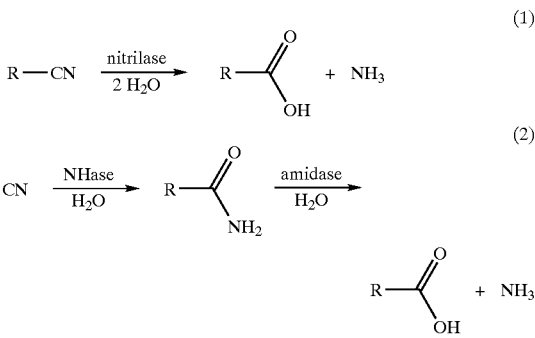

The prior art indicates that a microbial catalyst having a single nitrilase enzyme effects the reaction and is preferred (Webster et al., supra). Additionally, previously known processes require that the reaction be monitored throughout to maintain a low concentration of nitrile.

In the present invention, a microbial catalyst having a combination of nitrile hydratase and amidase activities has been identified which can produce acrylic acid and methacrylic acid from the corresponding nitriles at high concentration and with high specificity, and at complete conversion of the nitrile. The catalyst of the present invention does not require that the nitrile concentration be monitored over the course of the reaction to maintain a low concentration of nitrile, and does not require running the reaction at a low temperature (5–10° C.) in order to maintain the stability of the nitrile hydratase activity. Instead, the process uses a combination of thermostable nitrile hydratase and amidase enzymes as catalysts for the desired conversions.

The prior art teaches that acrylonitrile and methacrylonitrile can cause the inactivation of both nitrilase and nitrile hydratase activities of microbial catalysts. The hydrolysis or hydration reactions are routinely run at a low substrate concentration to avoid inactivation of the enzyme. In the present invention, the *C. testosteroni* 5-MGAM-4D catalyst utilizes two enzyme catalysts to convert acrylonitrile or methacrylonitrile to the corresponding acid. It was not known and could not be predicted that both the nitrile hydratase and amidase enzymes would be stable to the high concentrations of nitrile, amide and carboxylic acid present over the course of a single reaction, or over the course of a series of reactions when the catalyst was recycled to produce acrylic acid or methacrylic acid at high concentration.

Definitions:

In this disclosure, a number of terms and abbreviations are used. The following definitions apply unless specifically stated otherwise.

"Catalyst", "enzyme catalyst" or "microbial cell catalyst" refers to a catalyst that is characterized by a nitrilase activity or by a combination of nitrile hydratase and amidase activities. The catalyst may be in the form of an intact microbial cell, permeabilized microbial cell(s), one or more cell components of a microbial cell extract, partially-purified enzyme (s), or purified enzyme(s).

The terms "*Comamonas testosteroni*" and "*C. testosteroni*" are used interchangeably.

The term "acrylonitrile" is synonymous with cyanoethene, cyanoethylene, 2-propenenitrile, propenenitrile, vinyl cyanide, and all other synonyms of CAS Registry Number 107-13-1.

The term "acrylic acid" is synonymous with acroleic acid, ethylenecarboxylic acid, 2-propenoic acid, propenoic acid, vinylformic acid, and all other synonyms of CAS Registry Number 79-10-7.

The term "methacrylonitrile" is synonymous with 2-methyl-2-propenenitrile, α-methacrylonitrile, α-methylacrylonitrile, 1-methylethenyl cyanide, 2-cyano-1-propene, 2-cyanopropene, 2-methyl-2-propenenitrile, 2-methylacrylonitrile, 2-methylpropenenitrile, isobutenenitrile, isopropene cyanide, isopropenylnitrile, methacrylonitrile, methylacrylonitrile, and all other synonyms of CAS Registry Number 126-98-7.

The term "methacrylic acid" is synonymous with 2-methyl-2-propenoic acid, α-methacrylic acid, α-methylacrylic acid, 2-methyl-2-propenoic acid, 2-methylacrylic acid, methylacrylic acid, and all other synonyms of CAS Registry Number 79-41-4.

The term "suitable aqueous reaction mixture" refers to the materials and water in which the nitrile substrate and enzyme catalyst come into contact. Components of suitable aqueous reaction mixtures are referred to herein and those skilled in the art appreciate the range of component variations suitable for this process.

The abbreviations in the specification correspond to units of measure, techniques, properties, or compounds as follows: "sec" means second(s), "min" means minute(s), "h" means hour(s), "d" means day(s), "mL" means milliliters, "L" means liters, "mM" means millimolar, "M" means molar, "mmol" means millimole(s), and "wt" means weight. "HPLC" means high performance liquid chromatography, "ca" means approximately, "O.D." means optical density at the designated wavelength, "IU" means International Units.

DESCRIPTION OF THE PREFERRED EMBODIMENTS

Methods and Materials

Growth of Microbial Enzyme Catalysts

*Comamonas testosteroni* 5-MGAM-4D (ATCC 55744) was enriched from soil collected in Orange, Tex., U.S.A., using standard enrichment procedures with E2 basal medium (Table 1) (pH 7.2).

TABLE 1

| E2 Basal Medium g/L | | | |
|---|---|---|---|
| $KH_2PO_4$ | 1.4 | $NaMoO_4 \cdot 2H_2O$ | 0.0025 |
| $NaH_2PO_4$ | 6.9 | $NiCl_2 \cdot 6H_2O$ | 0.01 |
| KCl | 0.5 | $CuSO_4 \cdot 2H_2O$ | 0.005 |
| $MgSO_4 \cdot 7H_2O$ | 0.5 | Biotin | 0.0002 |
| $CaCl_2$ | 0.025 | folic acid | 0.0002 |
| NaCl | 1 | pyridoxine.HCl | 0.001 |
| sodium citrate | 0.1 | Riboflavin | 0.0005 |
| $FeSO_4 \cdot 7H_2O$ | 0.05 | nicotinic acid | 0.0005 |
| $CoCl_2 \cdot 6H_2O$ | 0.01 | Pantothenic acid | 0.0005 |
| $MnCl_2 \cdot 4H_2O$ | 0.001 | Vitamin B12 | 0.00001 |
| $ZnCl_2$ | 0.0005 | p-aminobenzoic acid | 0.0005 |
| $H_3BO_3$ | 0.000062 | | |

Table 2 contains modifications that were made to the E2 basal medium for the enrichment described above. Frozen 15% glycerol stocks were maintained at −65° C. to −70° C.

TABLE 2

| Strain | Enrichment Nitrile | Other |
|---|---|---|
| *Comamonas testosteroni* 5-MGAM-4D | 0.2% 2-methylglutaramide | pH 5.6 |

*Comamonas testosteroni* 5-MGAM-4D was grown aerobically under the following conditions (Table 3) for testing nitrile transformation activity.

TABLE 3

| Strain | Nitrile/Amide | Medium | ° C. | Time, h |
|---|---|---|---|---|
| 5-MGAM-4D | 0.2% (w/v) propionamide | E2, 0.6% (w/v) glucose + $Na_2$succinate.$2H_2O$ | 30 | 29 |

Harvested cells were frozen at −65 to −70° C. until used for nitrile transformation.

Use of *Comamonas testosteroni* 5-MGAM-4D for Production of Acrylic Acid and Methacrylic Acid

*Comamonas testosteroni* 5-MGAM-4D microbial cells contain a thermally unstable nitrile hydratase, in addition to a thermostable nitrile hydratase and amidase (U.S. Pat. No. 5,922,589). Heating a suspension of *Comamonas testosteroni* 5-MGAM-4D in a suitable buffer at 35–70° C. for between 10 and 120 minutes deactivates the thermally unstable nitrile hydratase activity of the microbial cell catalyst, without producing a significant decrease in the thermostable nitrile hydratase and amidase activities (U.S. Pat. No. 5,814,508). This heat-treatment procedure can be used in the present invention to prepare an enzyme catalyst without the thermally unstable nitrile hydratase, but is not necessary in the present application. Enzymatic activity of the untreated or heat-treated microbial catalysts are sustained in a stable state for a prolonged period of time.

Intact microbial cells having nitrile hydratase and amidase activities can be used as catalyst without any pretreatment such as permeabilization. Alternatively, the microbial cells may be permeabilized by methods familiar to those skilled in the art (e.g., treatment with toluene, detergents, or freeze thawing) to improve the rate of diffusion of materials into and out of the cells. Additionally, the catalyst may be in the form of microbial cells transformed to express *Comamonas testosteroni* 5-MGAM-4D nitrile hydratase and amidase activities.

The enzyme catalyst can be immobilized in a polymer matrix (e.g., alginate, carrageenan, polyvinyl alcohol, or polyacrylamide gel (PAG)) or on a soluble or insoluble support (e.g., celite) to facilitate recovery and reuse of the catalyst. Methods to immobilize cells in a polymer matrix or on a soluble or insoluble support have been widely reported and are well known to those skilled in the art. The enzyme activity or activities can also be isolated from the microbial cells and used directly as catalyst, or the enzyme activity or activities can be immobilized in a polymer matrix or on a soluble or insoluble support. These methods have also been widely reported and are well known to those skilled in the art (Methods in Biotechnology, Vol. 1: Immobilization of Enzymes and Cells; Gordon F. Bickerstaff, Editor; Humana Press, Totowa, N.J., USA; 1997).

The concentration of enzyme catalyst in the reaction mixture depends on the specific catalytic activity of the enzyme catalyst and is chosen to obtain the desired rate of reaction. The wet cell weight of the microbial cell catalyst in hydrolysis reactions typically ranges from 0.001 g to 0.100 g of wet cells per mL of total reaction volume, preferably from 0.002 g to 0.050 g of wet cells per mL. The specific activity of the microbial cell catalyst (IU/gram wet cell wt.) is determined by measuring the rate of acrylonitrile or methacrylonitrile hydration (for nitrile hydratase activity) or acrylamide or methacrylamide hydrolysis (for amidase activity) of a 0.30 M solution of the appropriate substrate at 25° C., using a known weight of the microbial cell catalyst. An IU of enzyme activity is defined as the amount of enzyme activity required to convert one micromole of substrate to product per minute.

The temperature of the hydrolysis reaction is chosen to optimize both the reaction rate and the stability of the enzyme catalyst activity. The temperature of the reaction may range from just above the freezing point of the suspension (ca. 0° C.) to 70° C., with a preferred range of reaction temperature of from 5° C. to 35° C. Reactions employing the enzyme catalyst may be run unbuffered in water, or in an aqueous reaction mixture containing a buffer (e.g., sodium or potassium phosphate), where the initial pH of the reaction is between 5.0 and 10.0, and preferably between 6.0 and 8.0. As the reaction proceeds, the pH of the reaction mixture may change due to the formation of an ammonium salt of acrylic acid or methacrylic acid by the hydrolysis of the nitrile functionality of acrylonitrile or methacrylonitrile, respectively. The reaction can be run to complete conversion of acrylonitrile or methacrylonitrile with no pH control, or in the presence of added buffer to control pH, or a suitable acid or base can be added over the course of the reaction to maintain the desired pH.

The concentration of acrylonitrile or methacrylonitrile in the reaction mixture may range from 1 mM to 7.5 M, preferably between 100 mM and 4 M, and most preferably between 1 M and 3 M. The acrylonitrile or methacrylonitrile may be added to a suitable reaction mixture in one portion, or may be added continuously as the nitrile is hydrolyzed to maintain a low concentration of the nitrile over the course of the reaction, thus limiting any potential inhibitory affects of the starting material or products on the nitrile hydratase activity.

The acrylic acid or methacrylic acid thus obtained may be isolated by treating the reaction mixture (from which insoluble matter including the cells has been removed) by procedures well known to those of ordinary skill. Such procedures include but are not limited to concentration, ion exchange, distillation, electrodialysis, extraction, and crystallization. The product may be isolated as the ammonium salt or (after acidification) as the corresponding carboxylic acid.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

In the following Examples, the percent recovery of methacrylonitrile or acrylonitrile, and the percent yields of the corresponding amide and carboxylic acid products were based on the initial concentration of methacrylonitrile or acrylonitrile present in the reaction mixture, and were determined by HPLC using a refractive index detector. Analyses for methacrylic acid, methacrylamide, and methacrylonitrile were performed using a Supelco LC-18-DB column (15 cm×4.6 mm dia.) with precolumn at 25° C. and 10 mM acetic acid, 10 mM sodium acetate in 7.5% methanol in water as eluent at 1.5 mL/min. Analyses for acrylic acid, acrylonitrile, and acrylamide were performed by HPLC using a Bio-Rad HPX-87H organic acid analysis column (30 cm×7.8 mm dia.) with precolumn at 50° C. and 0.010 N $H_2SO_4$ as eluent at 1 mL/min.

Example 1

Hydrolysis of Methacrylonitrile to Methacrylic Acid by *Comamonas testosteroni* 5-MGAM-4D Cells A suspension of 0.76 g (wet cell paste) *Comamonas testosteroni* 5-MGAM-4D cells (ATCC 55744) in 5.16 mL of distilled, deionized water (unbuffered) was placed into a 15-mL polypropylene centrifuge tube, then 40.2 mg of methacrylonitrile (0.10 M final concentration of methacrylonitrile in the suspension) was added and the resulting suspension mixed on a rotating platform at 25° C. Samples for analysis (0.180 mL) were mixed with 0.020 mL of 0.2 M butyric acid (HPLC external standard), centrifuged, and the supernatant analyzed by HPLC for methacrylonitrile, methacrylamide, and methacrylic acid. After 2 h, the yield of methacrylic acid was 100%, with no methacrylamide or methacrylonitrile remaining.

After complete conversion of 0.10 M methacrylonitrile at 2 h reaction time, an additional 121 mg of methacrylonitrile was added to the reaction mixture (0.40 M total methacrylonitrile), and after an additional 2 h, the yield of methacrylic acid was 100% (0.40 M methacrylic acid final concentration), with no methacrylamide or methacrylonitrile remaining.

After complete conversion of 0.40 M methacrylonitrile at 4 h total reaction time, an additional 241 mg of methacrylonitrile was added (1.0 M total methacrylonitrile added to the reaction mixture), and after an additional 15 h, the yield of methacrylic acid was 100% (1.0 M methacrylic acid final concentration), with no methacrylamide or methacrylonitrile remaining.

Example 2

Immobilization of *Comamonas testosteroni* 5-MGAM-4D Cells in Calcium Alginate

Example 2 illustrates a typical immobilization of cells in GA/PEI-crosslinked calcium alginate.

Into a 250-mL media bottle equipped with magnetic stir bar and containing 68.7 g of distilled, deionized water at 50° C. was slowly added 3.30 g of FMC BioPolymer Protanal® LF 10/60 alginate with rapid stirring. The mixture was heated to 75–80° C. with rapid stirring until the alginate was completely dissolved, and the resulting solution cooled to 25° C. in a water bath. To the alginate suspension was added 47.62 g of *Comamonas testosteroni* 5-MGAM-4D wet cell paste (19% dry cell weight) and 0.38 mL of distilled water with stirring. The cell/alginate mixture was added dropwise by syringe to 640 mL of 0.20 M calcium acetate buffer (pH 7.0) at 25° C. with stirring. After stirring for 2 h, the buffer was decanted from the resulting beads, which were resuspended in 217 mL of 0.20 M calcium acetate buffer (pH 7.0) at 25° C. With stirring, 4.45 g of 25 wt % glutaraldehyde (GA) in water was added and the beads mixed for 1.0 h zat 25° C. To the suspension was then added 17.8 g of 12.5 wt % polyethylenimine (PEI) (BASF Lupasol® PR971L, average molecular weight ca. 750,000) in water, and the beads mixed for an additional 1 h at 25° C. The crosslinked beads were then washed twice with 270 mL of 0.20 M calcium acetate buffer (pH 7.0) at 25° C., and stored in this same buffer at 5° C.

Example 3

Hydrolysis of Methacrylonitrile (1.0 M) by Immobilized *Comamonas testosteroni* 5-MGAM-4D Cells (No Buffer)

Into a 50-mL jacketed reaction vessel equipped with an overhead stirrer (temperature-controlled at 25° C. with a recirculating temperature bath) was placed 4.0 g of GA/PEI-crosslinked *Comamonas testosteroni* 5-MGAM-4D cell/alginate beads prepared as described in Example 2. To the reaction vessel was added 14.1 mL of distilled, deionized water, 0.2 mL of 0.20 M calcium acetate buffer (pH 7.0, 2.0 mM final calcium ion concentration in reaction mixture) and 1.68 mL (1.34 g, 1.0 M) of methacrylonitrile, and the mixture stirred at 25° C. Samples (0.100 mL) of the reaction mixture were mixed with 0.400 mL of water, and then 0.200 mL of the diluted sample was mixed with 0.200 mL of 0.200 M sodium butyrate (HPLC external standard) in water and 0.020 mL of 6.0 N hydrochloric acid. The resulting sample was centrifuged, and the supernatant analyzed by HPLC. After 105 min, the conversion of methacrylonitrile was 100%, and the yields of methacrylic acid and methacrylamide were 99.8% and 0%, respectively. At the completion of the reaction, the final concentration of methacrylic acid in the final product mixture was 1.0 M (8.6 wt %).

At the end of the reaction the product mixture was decanted from the catalyst beads, and an additional 14.1 mL of distilled, deionized water, 0.2 mL of 0.20 M calcium acetate buffer (pH 7.0, 2.0 mM final calcium ion concentration in reaction mixture) and 1.68 mL (1.34 g, 1.0 M) of methacrylonitrile mixed with the immobilized-cell catalyst at 25° C. After 150 min, the conversion of methacrylonitrile was 100%, and the yields of methacrylic acid and methacrylamide were 100% and 0%, respectively. At the completion of the second reaction with catalyst recycle, the final concentration of methacrylic acid in the final product mixture was 1.25 M (10.8 wt %).

At the end of the second reaction, the product mixture was decanted from the catalyst beads, and an additional 14.1 mL of distilled, deionized water, 0.2 mL of 0.20 M calcium acetate buffer (pH 7.0, 2.0 mM final calcium ion concentration in reaction mixture) and 1.68 mL (1.34 g, 1.0 M) of methacrylonitrile mixed with the immobilized-cell catalyst at 25° C. After 240 min, the conversion of methacrylonitrile was 100%, and the yields of methacrylic acid and methacrylamide were 100% and 0%, respectively. At the completion of the third reaction with catalyst recycle, the final concentration of methacrylic acid in the final product mixture was 1.35 M (11.6 wt %).

Example 4

Hydrolysis of Acrylonitrile (1.0 M to 3.0 M) by Immobilized *Comamonas testosteroni* 5-MGAM-4D Cells (No Buffer)

Into a 50-mL jacketed reaction vessel equipped with an overhead stirrer (temperature-controlled at 25° C. with a recirculating temperature bath) was placed 4.0 g of GA/PEI-crosslinked *Comamonas testosteroni* 5-MGAM-4D cell/alginate beads prepared as described in Example 2. To the reaction vessel was added 14.5 mL of distilled, deionized water, 0.2 mL of 0.20 M calcium acetate buffer (pH 7.0, 2.0 mM final calcium ion concentration in reaction mixture), and 1.32 mL (1.06 g, 1.0 M) of acrylonitrile, and the mixture stirred at 25° C. Samples (0.100 mL) of the reaction mixture were mixed with 0.400 mL of water, and then 0.200 mL of the diluted sample was mixed with 0.200 mL of 0.200 M sodium butyrate (HPLC external standard) in water and 0.020 mL of 6.0 N hydrochloric acid. The resulting sample was centrifuged, and the supernatant analyzed by HPLC. After 120 min, the conversion of acrylonitrile was 100%, and the yields of acrylic acid and acrylamide were 99.7% and 0%, respectively. At the completion of the reaction, the final concentration of acrylic acid in the final product mixture was 0.997 M (7.2 wt %).

At the end of the first reaction, the product mixture was decanted from the catalyst beads, and an additional 14.1 mL of distilled, deionized water, 0.2 mL of 0.20 M calcium acetate buffer (pH 7.0, 2.0 mM final calcium ion concentration in reaction mixture) and 1.32 mL (1.06 g, 1.0 M) of acrylonitrile mixed with 4.3 g of reaction heel (immobilized-cell catalyst and remaining product mixture from the first reaction) at 25° C. After 120 min, the conversion of acrylonitrile was 100%, and the yields of acrylic acid and acrylamide were 99.2% and 0%, respectively. At the completion of the second reaction with catalyst recycle, the final concentration of acrylic acid in the final product mixture was 1.20 M (8.6 wt %).

At the end of the second reaction, the product mixture was decanted from the catalyst beads, and an additional 12.8 mL of distilled, deionized water, 0.2 mL of 0.20 M calcium acetate buffer (pH 7.0, 2.0 mM final calcium ion concentration in reaction mixture) and 2.64 mL (2.12 g, 2.0 M) of acrylonitrile mixed with 4.4 g of reaction heel (immobilized-cell catalyst and remaining product mixture from the second reaction) at 25° C. After 210 min, the conversion of acrylonitrile was 100%, and the yields of acrylic acid and methacrylamide were 99.2% and 0.8%, respectively. At the completion of the third reaction with catalyst recycle, the final concentration of acrylic acid in the final product mixture was 2.24 M (16.1 wt %).

At the end of the third reaction, the product mixture was decanted from the catalyst beads, and an additional 11.4 mL of distilled, deionized water, 0.2 mL of 0.20 M calcium acetate buffer (pH 7.0, 2.0 mM final calcium ion concentration in reaction mixture) and 3.96 mL (3.18 g, 3.0 M) of acrylonitrile mixed with 4.4 g of reaction heel (immobilized-cell catalyst and remaining product mixture from the third reaction) at 25° C. After 18 h (overnight), the conversion of acrylonitrile was 100%, and the yields of acrylic acid and methacrylamide were 99.0% and 1.0%, respectively. At the completion of the fourth reaction with catalyst recycle, the final concentration of acrylic acid in the final product mixture was 3.58 M (25.8 wt %).

What is claimed is:

1. A process for producing methacrylic acid from methacrylonitrile comprising (a) contacting methacrylonitrile in a suitable aqueous reaction mixture with a catalyst characterized by a nitrile hydratase activity and an amidase activity of *Comamonas testosteroni* 5-MGAM-4D (ATCC 55744); and (b) isolating the methacrylic acid produced in (a) in the from of a salt or acid.

2. The process of claim 1 wherein the catalyst is in the form of microbial cells transformed to express *Comamonas testosteroni* 5-MGAM-4D nitrile hydratase and amidase activities.

3. The process of claim 1 further comprising before step (a) heating the catalyst of *Comamonas testosteroni* 5-MGAM-4D (ATCC 55744) to a temperature of about 35° C. to 70° C. for between 10 and 120 minutes, whereby thermally unstable nitrile hydratase activity is inactivated, and thermostable nitrile hydratase and amidase activities are preserved.

4. A process for producing acrylic acid from acrylonitrile comprising
    (a) contacting acrylonitrile in a suitable aqueous reaction mixture with an catalyst characterized by a nitrile hydratase and amidase activity of *Comamonas testosteroni* 5-MGAM-4D (ATCC 5744); and
    (b) isolating the acrylic acid produced in (a) in the form of a salt or acid.

5. The process of claim 4 wherein the catalyst is in the form of microbial cells transformed to express *Comamonas testosteroni* 5-MGAM-4D nitrile hydratase and amidase activities.

6. The process of claim 4 further comprising before step (a) heating the catalyst of *Comamonas testosteroni* 5-MGAM-4D (ATCC 55744) to a temperature of about 35° C. to 70° C. for between 10 and 120 minutes, whereby a thermally unstable nitrile hydratase activity is inactivated, and the thermostable nitrile hydratase and amidase activities are preserved.

\* \* \* \* \*

UNITED STATES PATENT AND TRADEMARK OFFICE
CERTIFICATE OF CORRECTION

PATENT NO. : 6,670,158 B2
DATED : December 30, 2003
INVENTOR(S) : Dicosimo, Robert et al.

It is certified that error appears in the above-identified patent and that said Letters Patent is hereby corrected as shown below:

Title page,
Item [54], Title, after "METHACRYLIC ACID" please insert -- AND --.
Item [75], Inventors, please change "Dicosimo" to read -- DiCosimo --.

Signed and Sealed this

Twenty-second Day of March, 2005

JON W. DUDAS
*Director of the United States Patent and Trademark Office*